United States Patent
Adams et al.

(10) Patent No.: US 11,150,245 B2
(45) Date of Patent: Oct. 19, 2021

(54) USE OF CIRCULATING TUMOR CELL MITOTIC INDEX IN CANCER STRATIFICATION AND DIAGNOSTICS

(71) Applicant: CREATV MICROTECH INC., Potomac, MD (US)

(72) Inventors: Daniel Adams, Basking Ridge, NJ (US); Cha-Mei Tang, Potomac, MD (US)

(73) Assignee: Creatv Microtech, Inc., Potomac, MD (US)

( * ) Notice: Subject to any disclaimer, the term of this patent is extended or adjusted under 35 U.S.C. 154(b) by 261 days.

(21) Appl. No.: 15/576,472

(22) PCT Filed: May 26, 2016

(86) PCT No.: PCT/US2016/034261
§ 371 (c)(1),
(2) Date: Nov. 22, 2017

(87) PCT Pub. No.: WO2016/191532
PCT Pub. Date: Dec. 1, 2016

(65) Prior Publication Data
US 2018/0156801 A1    Jun. 7, 2018

Related U.S. Application Data

(60) Provisional application No. 62/330,529, filed on May 2, 2016, provisional application No. 62/166,499, filed on May 26, 2015.

(51) Int. Cl.
*G01N 33/574* (2006.01)
*G01N 33/50* (2006.01)

(52) U.S. Cl.
CPC ....... *G01N 33/574* (2013.01); *G01N 33/5005* (2013.01); *G01N 33/5091* (2013.01); *G01N 33/5743* (2013.01); *G01N 33/57415* (2013.01); *G01N 33/57423* (2013.01); *G01N 33/57434* (2013.01); *G01N 33/57438* (2013.01); *G01N 33/57446* (2013.01); *G01N 2800/52* (2013.01); *G01N 2800/56* (2013.01); *G01N 2800/7028* (2013.01)

(58) Field of Classification Search
CPC ................................................ G01N 33/57415
See application file for complete search history.

(56) References Cited

FOREIGN PATENT DOCUMENTS

| JP | 2002-529704 | 9/2002 |
| JP | 2011-505012 | 2/2011 |
| WO | 2000/26666 | 5/2000 |
| WO | 2009/070392 | 6/2009 |
| WO | 2013/181532 | 12/2013 |

OTHER PUBLICATIONS

Haber et al. "Blood-Based Analyses of Cancer: Circulating Tumor Cells and Circulating Tumor DNA" May 6, 2014, Cancer Discovery, Jun. 2014: pp. 650-661. (Year: 2014).*
Hou et al. "Evaluation of Circulating Tumor Cells and Serological Death Biomarkers in Small Cell Lung Cancer Patients Undergoing Chemotherapy" (2009), American Journal of Pathology, vol. 175, No. 2: 808-816. (Year: 2009).*
Tryfonidis et al., "Detection of Circulating Cytokeratin-19 mRNA-Positive Cells in the Blood and the Mitotic Index of the Primary Tumor Have Independent Prognostic Value in Early Breast Cancer", Clinical Breast Cancer, 14(6): 442-450 (2014).
Spiliotaki et al., "Evaluation of proliferation and apoptosis markers in circulating tumor cells of women with early breast cancer who are candidates for tumor dormancy", Breast Cancer Research, 16(6): 485, pp. 1-13 (2014).
Raimondi et al., "Epithelial-mesenchymal transition and stemness features in circulating tumor cells from breast cancer patients", Breast Cancer Research and Treatment, 130(2): 449-455 (2011).
Rossi et al., "Prognostic impact of discrepant Ki67 and mitotic index on hormone receptor-positive, HER2-negative breast carcinoma", British Journal of Cancer, 113(7): 996-1002 (2015).
International Search Report and Written Opinion of the International Searching Authority, dated Aug. 22, 2016 in corresponding International Application No. PCT/US2016/034261.
Yuan et al., "Quantum Dots-Based Quantitative and In Situ Multiple Imaging on Ki67 and Cytokeratin to Improve Ki67 Assessment in Breast Cancer", PLOS ONE, Apr. 9, 2015, 1-17.
Office Action dated Mar. 10, 2020 in Japanese Patent Application No. 2018-513737, with English-language translation.

* cited by examiner

*Primary Examiner* — Teresa E Knight
(74) *Attorney, Agent, or Firm* — Wenderoth, Lind & Ponack, LLP

(57) ABSTRACT

Circulating tumor cells (CTCs) are associated with metastasis of malignant solid tumors in a patient. Presented here is evidence that CTCs exhibit cell cycle phase variability and that there is a strong correlation between the number of CTCs in a mitotic cell cycle phase and the prospects for long term survival of the subject from which the cells were obtained. Also presented herein are methods of determining the mitotic cell cycle phase of CTCs from a patient having cancer and using the information in grading malignant solid tumors and predicting the likelihood of survival of the patient.

21 Claims, 5 Drawing Sheets

A.

B.

A.

B.

USE OF CIRCULATING TUMOR CELL MITOTIC INDEX IN CANCER STRATIFICATION AND DIAGNOSTICS

BACKGROUND OF INVENTION

When tumor cells break away from primary malignant solid tumors, they can penetrate into the blood or lymphatic circulation, and ultimately migrate into organs or tissue and form metastases. Such tumor cells are termed circulating tumor cells (CTCs) and they are found in up to 65-85% of patients with metastatic solid tumors, depending on the type of cancer.

Given that 90% of cancer-related deaths are caused by the metastatic process, detection and characterization of CTCs could prove critical in determining, inter alia, whether medical intervention is needed to block or slow the spread of cancer in a patient. However, clinical use of CTCs has been limited to date due to a variety of reasons, including CTC rarity in the circulation and the current inability to accurately distinguish highly aggressive cell types from less aggressive cell types [1-4].

Some studies have indicated that CTC enumeration can be used as an independent prognostic indicator of survival in patients with cancer, i.e. a high number of CTCs in the circulation equates to short term patient survival [2-4, 17-20]. Thus, CTCs may have clinical utility in that their numbers in a blood sample can be correlated with prognostic survival information and therapeutic response in late stage cancers [1-3, 19]. While it has been established that enumerating CTCs using the threshold of ≥5 CTC per sample is prognostically valuable, translating this information to direct treatment for improved patient survival has been difficult [1, 2, 12, 28].

For many years, CTC research has attempted to differentiate clinically relevant CTCs from CTCs playing no role in metastatic spread by analyzing mutation rates, proteomes, epithelial-to-mesenchymal transition, etc. to improve their clinical utility [2, 17, 19, 20, 28]. Recently, proteomic and genomic phenotyping of single CTCs has shown that they are a heterogeneous population of multiple complicated phenotypes [28, 29] and subtyping CTCs by biomarker heterogeneity is an ongoing area of study. However, the complex heterogeneity, low numbers of CTC per sample, and the fact that 20-35% of late stage patients have no measurable CTCs, are all confounding factors inhibiting clinical utility [1, 2, 4, 12, 19].

As cancer grading is a form of morphological classification, it has been suggested that characterizing CTC phenotypes may provide additional prognostic stratification in cancer patients [3, 21-23]. For example, pathological grading for cell differentiation, including assessing the mitotic index (MI) in tumor tissue biopsies, is the gold standard in cancer diagnostics, prognostics, and treatment, and an intricate part of tumor staging algorithms [1, 5-9]. Classifying filtered tumor cells is currently used by histopathologists to identify and grade cancer cells from a number of body fluids including urine (bladder) [10], lung aspirates (lung) [25], and cerebral spinal fluid (brain/neuron) [26], though it not commonly used for blood-based biopsies [3]. It has been recently shown that CTCs isolated from peripheral blood using specialized filters retain detailed cellular architecture, allowing for a more descriptive assessment of CTCs [3, 17, 18, 24]. Thus, such grading might be applied to filter-isolated CTCs.

The inability to provide detailed cytological assessment in CTCs has also led some groups to rely on the proliferation index (PI) in their quantification (i.e. MIB-1, PCNA, Ki-67, etc.) [11-14]. However, the use of PI biomarkers in cancer is a highly contested and controversial subject [13, 14].

The elucidation of additional CTC phenotypes and characteristics that define grades of disease and/or that are directly correlated patient survival could be used in combination with currently knowledge regarding CTC numbers in important methodologies, including cancer stratification and diagnostics. The present invention is directed to these and other relevant goals.

BRIEF SUMMARY OF INVENTION

The inventors have shown for the first time that circulating tumor cells (CTCs) isolated from a biological sample, such as peripheral blood, can have cell cycle phase variability. That is, when a population of CTCs is isolated from a biological sample, there is variability in the cell cycle phase of the cells, with some cells in a mitotic cell cycle phase (M phase) (e.g., prophase, metaphase, anaphase, telophase, or cytokinesis) and some cells in a non-mitotic cell cycle phase (e.g., resting phase or interphase).

The inventors have also found that when CTCs are isolated from a biological sample of a subject having cancer there is a strong correlation between both the number of mitotic CTCs in the sample and the mitotic index (MI) of the CTCs in the sample and the prospects for long term survival of the subject. As explained in detail below, when CTCs are found to be undergoing active cell division, long term survival of the subject is less likely. Therefore, both the absolute number of mitotic CTCs and the MI of CTCs isolated from a cancer patient can be used to make certain predictions concerning survival and certain decisions regarding treatment, and to monitor the effectiveness of a given treatment.

The present invention is derived from these discoveries and it is directed, in one group of embodiments, to methods for determining the MI of a population of CTCs.

Thus, and in a first embodiment, the invention is directed to a method for determining the mitotic index of a population of CTCs, wherein the method comprises:

(a) determining the cell cycle phase of each CTC in a population of CTCs, and (b) calculating a mitotic index for the population of CTCs, thereby determining the mitotic index of a population of CTCs.

In a second, related embodiment, the invention is directed to a method for determining the mitotic index of a population of CTCs, wherein the method comprises:

(a) obtaining a population of CTCs from a biological sample of a subject, (b) determining the cell cycle phase of each CTC in the population of CTCs, and (c) calculating a mitotic index for the population of CTCs, thereby determining the mitotic index of a population of CTCs.

In a third, related embodiment, the invention is directed to a method for determining the mitotic index of a population of CTCs, wherein the method comprises:

(a) isolating cells having a diameter of between about 7 and 25 microns from a biological sample of a subject, (b) identifying each CTC in the cells of (a) to form a population of CTCs, (c) determining the cell cycle phase of each CTC in the population of CTCs of (b), and (d) calculating a mitotic index for the population of CTCs of (c), thereby determining the mitotic index of a population of CTCs.

The present invention is also directed, in a further group of embodiments, to methods for predicting likelihood of survival in subjects having cancer.

Thus, and in a fourth embodiment, the invention is directed to a method for predicting likelihood of survival of a subject having cancer, wherein the method comprises:

(a) obtaining a population of CTCs from a biological sample of a subject having cancer, and (b) screening the population of CTCs for cells in a mitotic cell cycle phase, wherein when one or more CTCs is identified as being in a mitotic cell cycle phase, the subject is predicted to have a lower likelihood of survival in comparison to a subject having the same cancer that does not have one or more CTCs identified as being in a mitotic cell cycle phase, thereby predicting likelihood of survival of a subject having cancer.

In a fifth, related embodiment, the invention is directed to a method for predicting likelihood of survival of a subject having cancer, wherein the method comprises:

(a) isolating cells having a diameter of between about 7 and 25 microns from a biological sample of a subject having cancer, (b) identifying each CTC in the cells of (a) to form a population of CTCs, and (c) screening the population of CTCs for cells in a mitotic cell cycle phase, wherein when one or more CTCs is identified as being in a mitotic cell cycle phase, the subject is predicted to have a lower likelihood of survival in comparison to a subject having the same cancer that does not have one or more CTCs identified as being in a mitotic cell cycle phase, thereby predicting likelihood of survival of a subject having cancer.

In certain aspects of these embodiments, the likelihood of survival is over a two year period.

The present invention is also directed, in a further group of embodiments, to methods for grading malignant solid tumors of a subject.

Thus, and in a sixth embodiment, the invention is directed to a method for grading a malignant solid tumor in a subject, wherein the method comprises:

(a) obtaining a population of CTCs from a biological sample of a subject having a malignant solid tumor, and (b) screening the population of CTCs for cells in a mitotic cell cycle phase, wherein when one or more CTCs is identified as being in a mitotic cell cycle phase, the tumor of the subject is graded as aggressive, thereby grading a malignant solid tumor in a subject.

In a seventh, related embodiment, the invention is directed to a method for grading a malignant solid tumor in a subject, wherein the method comprises:

(a) isolating cells having a diameter of between about 7 and 25 microns from a biological sample of a subject having a malignant solid tumor, (b) identifying each CTC in the cells of (a) to form a population of CTCs, and (c) screening the population of CTCs for cells in a mitotic cell cycle phase, wherein when one or more CTCs is identified as being in a mitotic cell cycle phase, the tumor of the subject is graded as aggressive, thereby grading a malignant solid tumor in a subject.

The present invention is also directed, in a further group of embodiments, to methods for monitoring the effectiveness of treatment in a subject having cancer.

Thus, and in an eighth embodiment, the invention is directed to a method for monitoring the effectiveness of treatment in a subject having cancer, wherein the method comprises:

(a) obtaining a first population of CTCs from a first biological sample of a subject having cancer, (b) screening the first population for cells in a mitotic cell cycle phase, (c) administering a cancer treatment to the subject, (d) obtaining a second population of CTCs from a second biological sample of the subject after treatment, and (e) screening the second population for cells in a mitotic cell cycle phase, wherein an increase in the number of mitotic CTCs in the second population versus the first population, or an increase in the mitotic index calculated for the second population versus the first population, suggests the treatment is ineffective.

In an ninth embodiment, the invention is directed to a method for monitoring the effectiveness of treatment in a subject having cancer, wherein the method comprises:

(a) isolating cells having a diameter of between about 7 and 25 microns from a first biological sample of a subject having cancer, (b) identifying each CTC in the cells of (a) to form a first population of CTCs, (c) screening the first population for cells in a mitotic cell cycle phase, (d) administering a cancer treatment to the subject, (e) isolating cells having a diameter of between about 7 and 25 microns from a second biological sample of the subject after treatment, (f) identifying each CTC in the cells of (a) to form a second population of CTCs, and (g) screening the second population for cells in a mitotic cell cycle phase, wherein an increase in the number of mitotic CTCs in the second population versus the first population, or an increase in the mitotic index calculated for the second population versus the first population, suggests the treatment is ineffective.

In the relevant aspects and embodiments of the invention, the cell cycle phase is determined by examining the morphology of the CTC nuclei through means that include, but are not limited to, nuclear stains (e.g., DAPI dyes, Hoechst dyes, Sytox dyes, and propidium iodide dyes) and colorimetric stains (e.g., H&E, hematoxylin, kernechtrot dye, methyl green, and methylene blue).

The cell cycle phase may be determined to be a mitotic cell cycle phase (e.g., the cell is in prophase, prometaphase, metaphase, anaphase, telophase, or cytokinesis) or a non-mitotic cell cycle phase (e.g., the cell is in a resting phase or interphase). Similarly, a mitotic cell cycle phase may be prophase, prometaphase, metaphase, anaphase, telophase, or cytokinesis. CTCs determined to be in a mitotic phase (e.g., prophase, metaphase, anaphase, telophase, or cytokinesis) are termed "mitotic CTCs" herein. CTCs determined to be in a non-mitotic phase (e.g., resting phase or interphase) are termed "non-mitotic CTCs" herein.

In the relevant aspects and embodiments of the invention, the mitotic index (MI) is a ratio of the mitotic to non-mitotic CTCs in a sample. The MI is calculated by dividing the number of CTCs determined to be in a mitotic phase by the number of CTCs determined to be in a non-mitotic phase. Alternatively, the mitotic index is calculated by dividing the number of CTCs determined to be in a mitotic phase by the total number of CTCs in the population of CTCs being analyzed.

In the relevant aspects and embodiments of the invention, the CTCs are characterized or identified as being CTCs based on one or more characteristics that include, but are not limited to, cellular size, cellular morphology, nuclear morphology, and expression or lack of expression of selected markers. It should be understood that CTCs have different characteristics depending on the identity of the malignant solid tumor from which they are derived.

A characteristic size for all CTCs is a diameter of between about 7 and 25 microns.

Morphological characteristics for all CTCs include, but are not limited to, lack of nuclear segmentation into granules.

Markers for epithelial tumor (i.e., carcinoma) CTCs include, but are not limited to, the presence of one or more of: cytokeratin (CK) 8, CK18, CK19, EpCAM, EGFR, HER2, MUC-1, EphB4, CEA, CK5, CK6, CK7, CK14, CK16, CK17, CK20, PLZ4, PSMA, PSA, PDX-1, CXCR-4, and CDX2, and the absence of one or more of CD45, CD14, and CD31. Epithelial tumors include, but are not limited to, breast, prostate, lung, colorectal and pancreatic tumors.

Markers for melanoma CTCs include, but are not limited to, the presence of one or more of: CD146, Melanin, PAX3d, MLANA, TGFβ2, MCAM, ABCB4, CSPG4, MART-1, MAGE-A3, and GAlNAc-T.

Markers for sarcoma CTCs include, but are not limited to, the presence of one or more of: vimentin.

Markers for renal cell carcinoma CTCs include, but are not limited to, the presence of one or more of: vimentin, CD10, CK8, CK18, CK19, c-Kit, and E-cadherin.

The presence or absence of CTC markers can be determining using means that include, but are not limited to, labeled antibodies, cellular stains, chromogenic stains, in situ stains, and radiolabeling. In preferred aspects, CTC markers are determined using antibodies labeled with a fluorescent label, a chromogenic label, a radioactive label, or a chemiluminescent label.

In a specific aspect of relevant embodiments, the CTCs are epithelial tumor CTCs and they are characterized by expression of EpCAM and cytokeratins 8, 18, and 19, and lack of expression of CD45.

In the relevant aspects and embodiments of the invention, cells may be obtained and/or isolated from a biological sample of a subject. The biological sample may be, but is not limited to, peripheral blood, blood, lymph nodes, bone marrow, cerebral spinal fluid, tissue, and urine. The biological sample may be a fresh sample or a cryo-preserved sample that is thawed. In a preferred aspect, the biological sample is peripheral blood. In other aspects, the blood is antecubital-vein blood, inferior-vena-cava blood or jugular-vein blood.

In the relevant aspects and embodiments of the invention, the biological sample has a volume of between about 1 and 50 mL, preferably between about 5 and 15 mL. In certain aspects, the biological sample has a volume of at least about 7.5 mL.

In the relevant aspects and embodiments of the invention, cells may be obtained and/or isolated from a biological sample of a subject using one or more means selected from the group consisting of size exclusion methodology, immunocapture, red blood cell lysis, white blood cell depletion, FICOLL, electrophoresis, dielectrophoresis, flow cytometry and microfluidic chip, or a combination thereof. In a particular aspect, the size exclusion methodology comprises use of a microfilter. Suitable microfilters can have a variety of pore sizes and shapes. In certain aspects, the pore size ranges from about 5 microns to about 10 microns. The pores may have a round, race-track shaped, oval, square or rectangular pore shapes. The microfilter may have precision pore geometry and uniform pore distribution. In a particular aspect, cells are isolated using a CellSieve™ low-pressure microfiltration assay, where the filter comprises a photo-definable dry film. In other aspects, cells are isolated using a microfluidic chip based on physical size-based sorting, hydrodynamic size-based sorting, grouping, trapping, immunocapture, concentrating large cells, or eliminating small cells based on size.

In the relevant aspects and embodiments of the invention, cells can be characterized in the device used to collect the cells from a biological sample. For example, when CTCs are being identified in a population of the cells obtained from a biological sample, the phenotypic expression of cellular markers, such as EpCAM, cytokeratins 8, 18, 19, DAPI, and CD45 with respect to CTCs from epithelial tumors, can be determined without removing the cells from the devices. In a particular example and when microfilters are used to collect the cells, the cells can be characterizes as they lay on the surface of the microfilter. In other aspects and embodiments, the cells are removed from the device and then characterized. Further, the cells may be fixed or unfixed when being characterized.

In the relevant aspects and embodiments of the invention, the subject is a human, a non-human primate, bird, horse, cow, goat, sheep, a companion animal, such as a dog, cat or rodent, or other mammal.

In the relevant aspects and embodiments of the invention, the cancer is one or more of a lymphoma and a malignant solid tumor, such carcinoma, sarcoma, neuroblastoma, hepatoblastoma, retinoblastoma, or melanoma. Carcinomas are of epithelial origin and include, but are not limited to, breast cancer, prostate cancer, lung cancer, pancreatic cancer, and colorectal cancer. The solid tumor can be in Stage I, Stage II, Stage III, and/or Stage IV.

In the relevant aspects and embodiments of the invention, the malignant solid tumor may be carcinoma, sarcoma, neuroblastoma, hepatoblastoma, retinoblastoma, or melanoma. In particular, the solid tumor may be a breast tumor, a prostate tumor, a lung tumor, a pancreatic tumor, or a colorectal tumor.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

(FIG. 1B) CTC in Early Prophase with chromatin condensing seen as small dots in the nucleus; (FIG. 1C) CTC in Prophase with condensed chromatin and highly active mitochondria seen outside the nucleus as DAPI dots; (FIG. 1D) CTC in Prometaphase where chromatin can be seen condensing to the center of the CTC; (FIG. 1E) CTC in Metaphase with condensed chromatin lining up along the cell's axis; (FIG. 1F) CTC in Metaphase/Anaphase transition, the two chromatins can be seen beginning to separate along the cell plate; (FIG. 1G) CTC in Anaphase with the two chromosome sets seen moving to polar ends of the cell; (FIG. 1H) CTC in telophase is seen with two distinct cell envelopes and a contractile ring in the center of the cell; (FIG. 1I) CTC in Late Telophase/Cytokinesis as a contractile ring is pinching the cell into two cells but the chromatin remains condensed; (FIG. 1J) end of Cytokinesis as nuclear envelopes are reformed, the contractile ring almost complete and the chromatin has expanded. First column: merger of images from second through fifth columns; second column: nuclear staining with DAPI; third column: cytokeratin staining for CK 8, 18 and 19; fourth column: staining for EpCAM; fifth column: staining for CD45. Scale bar=15 µm.

FIG. 2A provides Kaplan-Meier estimates of probabilities of overall survival of breast cancer patients with <5 CTCs per sample (upper line) vs patients with ≥5 CTCs per sample (lower solid line). FIG. 2B provides Kaplan-Meier estimates of probabilities of overall survival of breast cancer patients with 0 mitotic CTCs per sample (upper line) vs patients with ≥1 mitotic CTC per sample (lower solid line). Samples were 7.5 mL peripheral blood.

FIG. 3A—"receptor positive" cells are those cells found to express each of ER, PR, and HER2; "triple negative" cells are those that lack expression of ER, PR, and HER2. FIG. 3B—"luminal A" and "luminal B" are established breast cancer subtypes; "triple negative" cells are those that lack expression of ER, PR, and HER2; "Her2+" cells are those that express HER2.

DETAILED DESCRIPTION OF THE INVENTION

I. Definitions

Figures 1A, 1B, 1C, 1D, 1E:
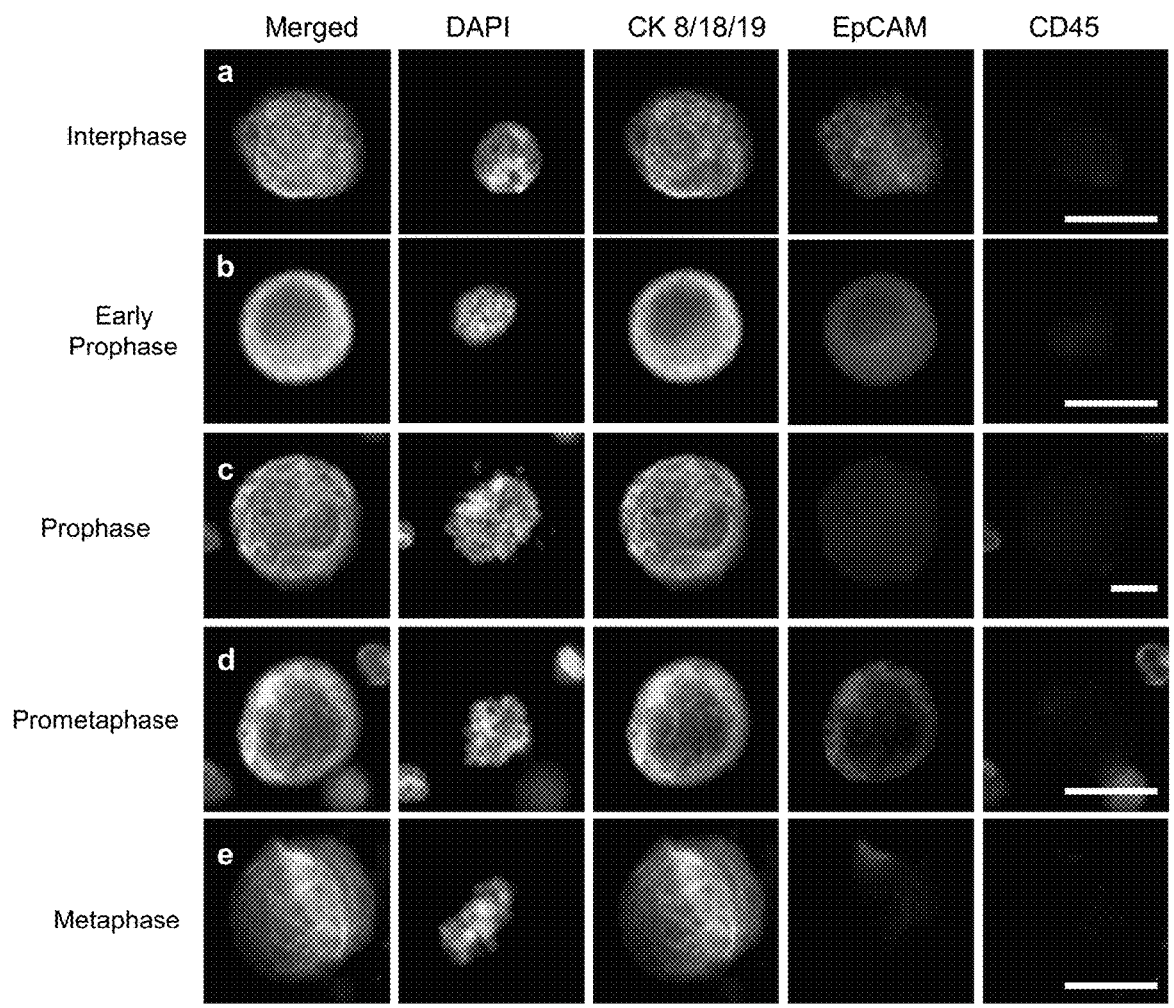
FIGS. 1A-1J. Common recognizable cytologies of CTCs in mitosis (M phase) isolated from breast cancer patients. The cells are stained for nucleus, cytokeratin 8, 18 and 19, EpCAM, and CD45. The markers are individually shown and images with the markers merged together are also shown. Representative images of (FIG. 1A) the "classical" EpCAM positive CTC in Interphase, i.e. not in mitosis.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/− 5-10% of the recited value) that one of ordinary skill in the art would consider equivalent to the recited value (e.g., having the same function or result). In some instances, the term "about" may include numerical values that are rounded to the nearest significant figure.

II. The Present Invention

Grading cancer is done by histopathological examination of a tissue biopsy extracted from suspicious tissue samples, primarily for use in cancer diagnosis [1, 5-9]. Secondary, histopathological examination allows for stratification of patients based on the morphology of the cells from the tissue (i.e., cell grade) for aiding patient assessment and treatment [1, 5-8]. Though many cancers are graded using differing grading systems (e.g. Gleason, Bloom and Richardson Nottingham) and there are issues with subjectivity and tumor heterogeneity, certain aspects are universal in pathological assessment of malignancy, such a mitotic index (MI) and cell differentiation [1, 5-9]. Mitosis in tumor cell grading, identified by specific cellular events occurring during cell division (e.g. prophase, metaphase, anaphase, telophase), is considered a primary predictor of survival and an indicator of therapy response [5-10].

CTCs are found in up to 65-85% of patients with metastatic disease, and they are used for prognostics by enumerating the number of cells in a sample (i.e., a high number of CTCs equates to shorter survival times), without any additional subtyping. Recently, the inventors found that filter-based isolation of CTCs produced cells that retain their detailed cellular architecture and the details of the cellular architecture can be visualized, allowing for classification as CTCs by morphology. As cancer grading is a form of morphology classification, the inventors considered that grading CTCs may provide additional prognostic stratification in cancer patients and aid in identifying aggressive CTC phenotypes. Classifying tumor cells post-filtration is currently used by histopathologists to identify and grade cancer cells from a number of body fluids including urine (bladder cancer), lung aspirates (lung cancer), and cerebral spinal fluid (brain/neuron cancer) via traditional methods. The inventors found that the same could be applied to CTCs.

As discussed in the examples below, experiments were conducted to determine whether a visual cytological assessment of cells in mitosis is applicable to CTCs. The mitotic status of CTCs was also evaluated to assess the prognostic value of enumerated CTCs and their mitotic indices. The resulting data indicate that applying histology-based determinations regarding the number of mitotic CTCs in a sample and/or mitotic indices of populations of CTCs can enhance patient stratification, and may provide an improvements in treatment decisions.

Thus, the present invention is directed to (i) methods for determining the MI of a population of CTCs, (ii) methods for predicting likelihood of survival in subjects having cancer, (iii) methods for grading malignant solid tumors of a subject, and (iv) methods for monitoring the effectiveness of treatment in a subject having cancer, among other important embodiments.

Methods for Determining the MI of a Population of CTCs

In one group of embodiments the invention is directed to methods for determining the mitotic index (MI) of a population of CTCs. The MI of a population of CTCs can be used in clinical applications that include screening a subject for cancer, screening a subject for cancer metastasis, screening a subject for recurrent of cancer, making prognostic determinations in a subject having cancer, monitoring the effectiveness of a cancer treatment, grading a tumor, and the other means and applications discussed herein.

In one embodiment, the invention is directed to a method for determining the mitotic index of a population of CTCs, wherein the method comprises:

(a) determining the cell cycle phase of each CTC in a population of CTCs, and (b) calculating a mitotic index for the population of CTCs, thereby determining the mitotic index of a population of CTCs.

In another embodiment, the invention is directed to a method for determining the mitotic index of a population of CTCs, wherein the method comprises:

(a) obtaining a population of CTCs from a biological sample of a subject, (b) determining the cell cycle phase of each CTC in the population of CTCs, and (c) calculating a mitotic index for the population of CTCs, thereby determining the mitotic index of a population of CTCs.

In a further embodiment, the invention is directed to a method for determining the mitotic index of a population of CTCs, wherein the method comprises:

(a) isolating cells having a diameter of between about 7 and 25 microns from a biological sample of a subject, (b) identifying each CTC in the cells of (a) to form a population of CTCs, (c) determining the cell cycle phase of each CTC in the population of CTCs of (b), and (d) calculating a mitotic index for the population of CTCs of (c), thereby determining the mitotic index of a population of CTCs.

Methods for Predicting Likelihood of Survival

In another group of embodiments the invention is directed to methods for predicting likelihood of survival in subjects having cancer. Such methods can be used alone in predicting the likelihood of survival for a subject having cancer, or used in combination with other means that provide relevant prognostic information. Such methods can simply be used to provide a subject having cancer with additional information relevant to their condition, or be used to assist a clinician in making decisions regarding appropriate courses of treatment.

In one embodiment, the invention is directed to a method for predicting likelihood of survival of a subject having cancer, wherein the method comprises:

(a) obtaining a population of CTCs from a biological sample of a subject having cancer, and (b) screening the population of CTCs for cells in a mitotic cell cycle phase, wherein when one or more CTCs is identified as being in a mitotic cell cycle phase, the subject is predicted to have a lower likelihood of survival in comparison to a subject having the same cancer that does not have one or more CTCs identified as being in a mitotic cell cycle phase, thereby predicting likelihood of survival of a subject having cancer.

In another embodiment, the invention is directed to a method for predicting likelihood of survival of a subject having cancer, wherein the method comprises:

(a) isolating cells having a diameter of between about 7 and 25 microns from a biological sample of a subject having cancer, (b) identifying each CTC in the cells of (a) to form a population of CTCs, and (c) screening the population of CTCs for cells in a mitotic cell cycle phase, wherein when one or more CTCs is identified as being in a mitotic cell cycle phase, the subject is predicted to have a lower likelihood of survival in comparison to a subject having the same cancer that does not have one or more CTCs identified as being in a mitotic cell cycle phase, thereby predicting likelihood of survival of a subject having cancer.

The likelihood of survival can be determined over selected periods of time including, but not limited to, a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 month period. In particular aspects, the selected period of time is a one year period, a two year period, or a three year period.

Methods for Grading Malignant Solid Tumors

In one group of embodiments the invention is directed to methods for grading malignant solid tumors of a subject. Such methods can be used, for example, to assist a clinician in making decisions regarding appropriate courses of treatment, based on the grade (e.g., aggressiveness) of a tumor.

In one embodiment, the invention is directed to a method for grading a malignant solid tumor in a subject, wherein the method comprises:

(a) obtaining a population of CTCs from a biological sample of a subject having a malignant solid tumor, and (b) screening the population of CTCs for cells in a mitotic cell cycle phase, wherein when one or more CTCs is identified as being in a mitotic cell cycle phase, the tumor of the subject is graded as aggressive, thereby grading a malignant solid tumor in a subject.

In another embodiment, the invention is directed to a method for grading a malignant solid tumor in a subject, wherein the method comprises:

(a) isolating cells having a diameter of between about 7 and 25 microns from a biological sample of a subject having a malignant solid tumor, (b) identifying each CTC in the cells of (a) to form a population of CTCs, and (c) screening the population of CTCs for cells in a mitotic cell cycle phase, wherein when one or more CTCs is identified as being in a mitotic cell cycle phase, the tumor of the subject is graded as aggressive, thereby grading a malignant solid tumor in a subject.

In additional to grading tumors as aggressive when one or more mitotic CTC is found, the tumors may alternatively be graded as a Grade III or a Grade IV tumor.

Methods for Monitoring the Effectiveness of Cancer Treatment

In one group of embodiments the invention is directed to methods for monitoring the effectiveness of treatment in a subject having cancer. Such monitoring can be used, for example, to assist a clinician in making decisions regarding whether a current course of treatment should be continued or if it has been sufficient, and whether a different course of treatment should be followed. These methods can utilize changes in the total number of mitotic CTCs present in samples obtained from a subject before and after treatment, or changes in the mitotic indices calculated for populations of CTCs present in samples obtained from a subject before and after treatment, or both.

In one embodiment, the invention is directed to a method for monitoring the effectiveness of treatment in a subject having cancer, wherein the method comprises:

(a) obtaining a first population of CTCs from a first biological sample of a subject having cancer, (b) screening the first population for cells in a mitotic cell cycle phase, (c) administering a cancer treatment to the subject, (d) obtaining a second population of CTCs from a second biological sample of the subject after treatment, and (e) screening the second population for cells in a mitotic cell cycle phase, wherein an increase in the number of mitotic CTCs in the second population versus the first population, or an increase in the mitotic index calculated for the second population versus the first population, suggests or otherwise indicates that the treatment is ineffective. In another embodiment, the invention is directed to a method for monitoring the effectiveness of treatment in a subject having cancer, wherein the method comprises:

(a) isolating cells having a diameter of between about 7 and 25 microns from a first biological sample of a subject having cancer, (b) identifying each CTC in the cells of (a) to form a first population of CTCs, (c) screening the first population for cells in a mitotic cell cycle phase, (d) administering a cancer treatment to the subject, (e) isolating cells having a diameter of between about 7 and 25 microns from a second biological sample of the subject after treatment, (f) identifying each CTC in the cells of (a) to form a second population of CTCs, and (g) screening the second population for cells in a mitotic cell cycle phase, wherein an increase in the number of mitotic CTCs in the second population versus the first population, or an increase in the mitotic index calculated for the second population versus the first population, suggests or otherwise indicates that the treatment is ineffective.

It should be understood that the first and second biological samples from the subject should be as similar as possible in characteristics (e.g., amount, source, storage conditions, treatment conditions, means for analysis), but that minor variations will still produce meaning results in terms of number of mitotic CTCs in the sample and MI calculations.

The embodiments and aspects of the invention described herein can be better understood by the following details.

As used herein, the cell cycle phase is the phase of cellular development in which a particular cell is found. The cell cycle generally comprises a resting/quiescent/senescent phase, interphase, and a cell division phase. Together, the resting phase and interphase are termed the "non-mitotic phase" or "non-mitotic cell cycle phase" herein. The cell division phase includes the various stages of mitosis (e.g., prophase, prometaphase, metaphase, anaphase, and telophase) and cytokinesis, together termed the "mitotic phase" or "mitotic cell cycle phase" herein.

The cell cycle phase may be determined for a selected cell by examining the morphology of the cellular nuclei to determine whether the cell is in a mitotic or non-mitotic phase. There are many well-established means for examining cellular nuclei that include, but are not limited to, nuclear stains (e.g., DAPI dyes, Hoechst dyes, Sytox dyes, and propidium iodide dyes) and colorimetric stains (e.g., H&E, hematoxylin, kernechtrot dye, methyl green, and methylene blue) followed by microscopic examination of the cells, whether by the human eye or electronic means.

The cell cycle phase may be determined to be a mitotic cell cycle phase (e.g., the cell is in prophase, prometaphase, metaphase, anaphase, telophase, or cytokinesis) or a non-mitotic cell cycle phase (e.g., the cell is in a resting phase or interphase). Similarly, a mitotic cell cycle phase may be prophase, prometaphase, metaphase, anaphase, telophase, or cytokinesis. CTCs determined to be in a mitotic phase (e.g., prophase, metaphase, anaphase, telophase, or cytokinesis) are termed "mitotic CTCs" herein. CTCs determined to be in a non-mitotic phase (e.g., resting phase or interphase) are termed "non-mitotic CTCs" herein.

The mitotic index (MI) is a ratio of the mitotic to non-mitotic CTCs in a sample. The MI may be calculated by dividing the number of CTCs determined to be in a mitotic phase by the number of CTCs determined to be in a non-mitotic phase. Alternatively, the mitotic index may be calculated by dividing the number of CTCs determined to be in a mitotic phase by the total number of CTCs in the population of CTCs being analyzed.

In the relevant aspects and embodiments of the invention, the CTCs are characterized or identified as being CTCs based on one or more characteristics that include, but are not limited to, cellular size, cellular morphology, nuclear morphology, and expression or lack of expression of selected markers. The identification of a particular cell as a CTC can be challenging in some instances because CTCs have different characteristics depending on the identity of the malignant solid tumor from which they are derived. That is, different combinations of cellular markers are used to identify CTCs in a biological sample depending on the identity of the cancer in the subject. However, a characteristic size for all CTCs regardless of cancer type is a diameter of between about 7 and 25 microns. Thus, the CTCs defined herein include cells having an average diameter of between about 7-24 microns, 7-23 microns, 7-22 microns, 7-21 microns, 7-20 microns, 7-19 microns, 7-18 microns, 7-17 microns, 7-16 microns, 7-15 microns, 7-14 microns, 7-13 microns, 7-12 microns, 7-11 microns, 8-24 microns, 9-24 microns, 10-24 microns, 11-24 microns, 12-24 microns, 13-24 microns, 14-24 microns, 15-24 microns, 16-24 microns, 17-24 microns, 18-24 microns, 19-24 microns, 20-24 microns, 21-24 microns, 22-24 microns, and 23-24 microns. Morphological characteristics for all CTCs also include lack of nuclear segmentation into granules.

Markers for epithelial tumor (i.e., carcinoma) CTCs include, but are not limited to, the presence of one or more of: cytokeratin (CK) 8, CK18, CK19, EpCAM, EGFR, HER2, MUC-1, EphB4, CEA, CK5, CK6, CK7, CK14, CK16, CK17, CK20, PLZ4, PSMA, PSA, PDX-1, CXCR-4, and CDX2, and the absence of one or more of CD45, CD14, and CD31. Epithelial tumors include, but are not limited to, breast, prostate, lung, colorectal and pancreatic tumors.

Markers for melanoma CTCs include, but are not limited to, the presence of one or more of: CD146, Melanin, PAX3d, MLANA, TGFβ2, MCAM, ABCB4, CSPG4, MART-1, MAGE-A3, and GAlNAc-T.

Markers for sarcoma CTCs include, but are not limited to, the presence of one or more of: vimentin.

Markers for renal cell carcinoma CTCs include, but are not limited to, the presence of one or more of: vimentin, CD10, CK8, CK18, CK19, c-Kit, and E-cadherin.

The presence or absence of CTC markers can be determining using labeling means that include, but are not limited to, labeled antibodies, cellular stains, chromogenic stains, in situ stains, and radiolabeling. In preferred aspects, CTC markers are determined using antibodies labeled with a fluorescent label, a chromogenic label, a radioactive label, or a chemiluminescent label. After exposing a cell or population of cells to selected labeling means, the presence or absence of the labels can be determined via microscopic examination of the cells, whether by the human eye or electronic means.

In a specific aspect of relevant embodiments, the CTCs are epithelial tumor CTCs and they are characterized by expression of EpCAM and cytokeratins 8, 18, and 19, and lack of expression of CD45.

Cells to be analyzed may be obtained and/or isolated from a biological sample of a subject. The biological sample may be, but is not limited to, peripheral blood, blood, lymph nodes, bone marrow, cerebral spinal fluid, tissue, and urine. When the biological sample is a tissue or other solid or semi-solid material, it can be processed in a manner that releases the cells contained herein. The biological sample may be a fresh sample or a cryo-preserved sample that is thawed. In a preferred aspect, the biological sample is peripheral blood. In other aspects, the blood is antecubital-vein blood, inferior-vena-cava blood or jugular-vein blood. The cells may subjected to normal and customary treatments, i.e., fixation, as part of the method of analysis.

In the relevant aspects and embodiments of the invention, the biological sample has a volume of between about 0.1 and 100 mL. The skilled artisan will understand that the volume of the biological sample is not critical to the methods disclosed herein. A convenient volume of 7.5 mL was used in the experiments described herein, and thus 7.5 mL has been shown to provide relevant data. However, when a low number of CTCs (e.g., less than about 5) is found is a given volume of a biological sample, the sample volume can be increased without departing from the spirit and scope of the methods disclosed herein. Other useful volumes include between about 1 and 100 mL, 1 and 90 mL, 1 and 80 mL, 1 and 70 mL, 1 and 60 mL, 1 and 50 mL, 1 and 40 mL, 1 and 30 mL, 1 and 22.5 mL, 1 and 20 mL, 1 and 15 mL, 1 and 10 mL, 1 and 9.5 mL, 1 and 9 mL, 1 and 8.5 mL, 1 and 8 mL, 1 and 7.5 mL, 1 and 7 mL, 1 and 6.5 mL, 1 and 6 mL, 1 and 5.5 mL, 1 and 5 mL, 1 and 4.5 mL, 1 and 4 mL, 1 and 3.5 mL, 1 and 3 mL, 1 and 2.5 mL, and between 1 and 2 mL. In a preferred aspect, the volume is between 5 and 15 mL. In certain aspects, the biological sample has a volume of at least about 22.5 mL, 15 mL, 10 mL, 9.5 mL, 9 mL, 8.5 mL, 8 mL, 7.5 mL, 7 mL, 6.5 mL, 6 mL, 5.5 mL, 5 mL, 4.5 mL, 4 mL, 3.5 mL, 3 mL, 2.5 mL, 2 mL, 1.5 mL, 1 mL or 0.5 mL.

The cells may be obtained and/or isolated from a biological sample of a subject using means well known in the art that include, but are not limited to, size exclusion methodology, immunocapture, red blood cell lysis, white blood cell depletion, FICOLL, electrophoresis, dielectrophoresis, flow cytometry and microfluidic chip, or a combination thereof.

In a particular aspect, the size exclusion methodology comprises use of a microfilter. Suitable microfilters can have a variety of pore sizes and shapes. In certain aspects, the pore size ranges from about 5 microns to about 10 microns. The pores may have a round, race-track shaped, oval, square or rectangular pore shapes. The microfilter may have precision pore geometry and uniform pore distribution. In a particular aspect, cells are isolated using a CellSieve™ low-pressure microfiltration assay, where the filter comprises a photo-definable dry film. In other aspects, cells are isolated using a microfluidic chip based on physical size-based sorting, hydrodynamic size-based sorting, grouping, trapping, immunocapture, concentrating large cells, or eliminating small cells based on size.

The cells can be characterized in the device used to collect the cells from a biological sample. For example, when CTCs are being identified in a population of the cells obtained from a biological sample, the phenotypic expression of cellular markers, such as EpCAM, cytokeratins 8, 18, 19, DAPI, and CD45 with respect to CTCs from epithelial tumors, can be determined without removing the cells from the devices. In a particular example and when microfilters are used to collect the cells, the cells can be characterizes as they lay on the surface of the microfilter. In other aspects and embodiments, the cells are removed from the device and then characterized. Further, the cells may be fixed or unfixed when being characterized.

As used herein, the subject is a human.

In the relevant aspects and embodiments of the invention, the cancer is one or more of a lymphoma and a malignant solid tumor, such carcinoma, sarcoma, neuroblastoma, hepatoblastoma, retinoblastoma, or melanoma. Carcinomas are of epithelial origin and include, but are not limited to, breast cancer, prostate cancer, lung cancer, pancreatic cancer, and colorectal cancer. The malignant solid tumor can be in Stage I, Stage II, Stage III, and/or Stage IV.

In the relevant aspects and embodiments of the invention, the malignant solid tumor may be carcinoma, sarcoma, neuroblastoma, hepatoblastoma, retinoblastoma, or melanoma. In particular, the solid tumor may be a breast tumor, a prostate tumor, a lung tumor, a pancreatic tumor, or a colorectal tumor.

III. EXAMPLES

Blood Sample Collection. 36 whole peripheral blood samples were drawn prospectively from women who were actively undergoing treatment for previously confirmed stage III or IV breast cancer, at either Fox Chase Cancer Center (FCCC) or University of Maryland, Baltimore (UMB) between 2011 and 2013. The study group characteristics can be found in Table 1. Anonymized peripheral blood samples were supplied through a collaboration agreement with FCCC and UMB, with written informed consent and according to the local IRB approval at each institution. In addition, healthy women volunteers donated blood samples (n=16) with written informed consent and IRB approval by Western Institutional Review Board, median age of 52. All anonymized blood samples were drawn into CellSave preservative tubes™ (~9 mL, Janssen Diagnostics). 7.5 mL of blood was used to enumerate CTCs using CellSieve™ microfiltration (Creatv MicroTech Inc.) at UMB, FCCC or Creatv Microtech. Results and patient identification from institutions were not shared or communicated until completion of study.

TABLE 1

| Category | Subcategory | Number of patients |
|---|---|---|
| Stage | 1 | — |
| | 2 | — |
| | 3 | 9 |
| | 4 | 27 |
| ER/PR* | Positive | 16 |
| | Negative | 17 |
| HER2* | Positive | 9 |
| | Negative | 24 |
| ER/PR/HER2* | Positive | 23 |
| | Negative | 10 |
| Treatment | Baseline | 5 |
| | 1$^{st}$ Line | 9 |
| | 2$^{nd}$ Line, or subsequent† | 22 |
| Pathological Grade | 1 | 1 |
| | 2 | 6 |
| | 3 | 19 |
| | ‡unknown | 10 |
| Histology | Ductal | 17 |
| | Lobular | 3 |
| | ‡other | 16 |

*3 of 36 patients had unknown receptor type; ER = estrogen receptor; PR = progesterone receptor; HER2 = human epidermal growth factor receptor 2.
†8 patients were not currently on therapy, but starting 2nd line treatment.
‡Tissue unavailable for histology assessment, and/or patients with unspecified metastatic breast cancer, and/or patients with cancers other than IDC or ILC.

Figures 1F, 1G, 1H, 1I, 1J:
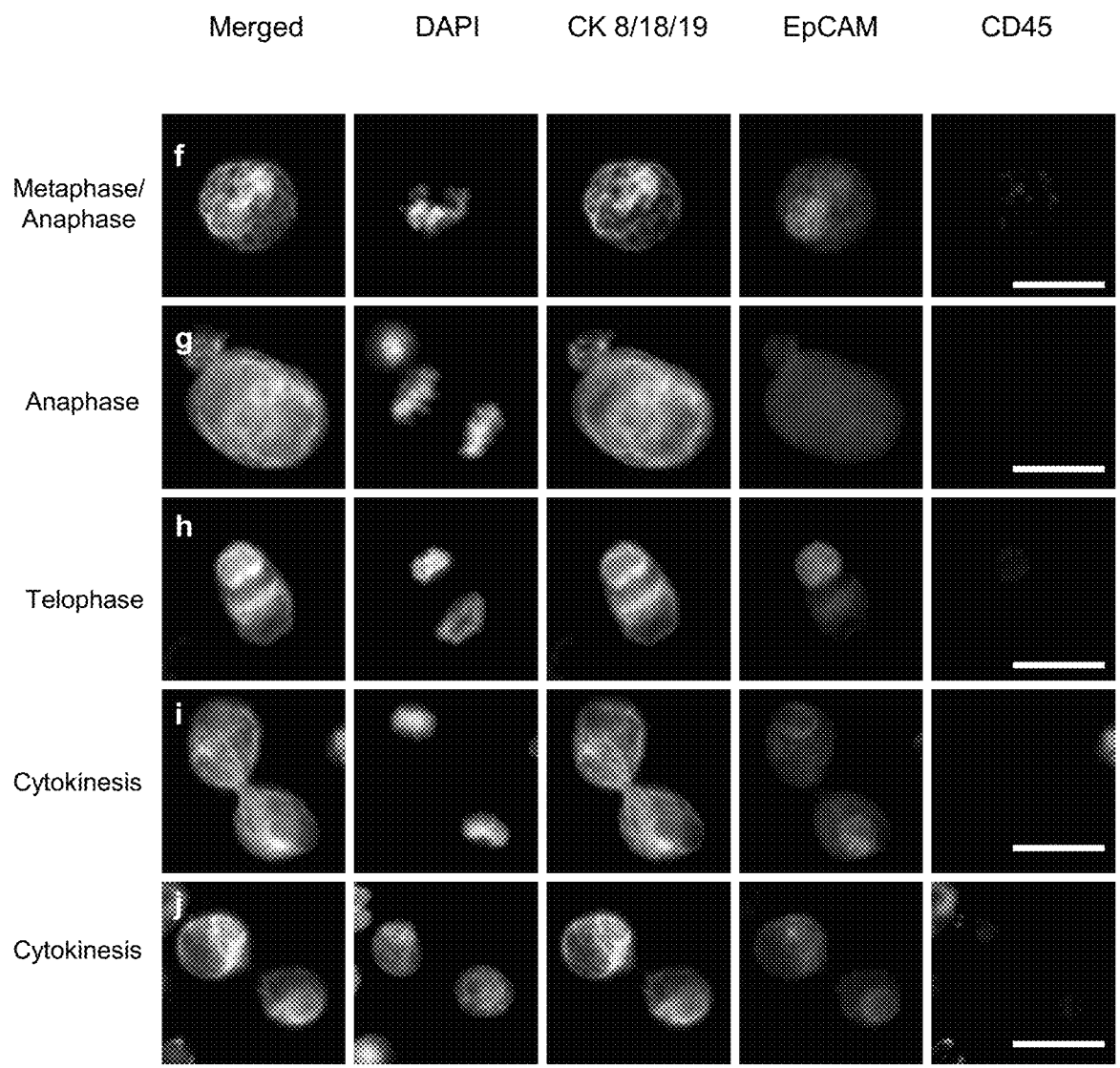

CellSieve™ Low-Flow Microfiltration Procedure. Samples were run at FCCC, UMB or Creatv MicroTech with a CellSieve™ Microfiltration Assay (Creatv MicroTech Inc.) using a low-pressure vacuum system [18]. CellSieve™ Microfiltration Assay isolates CTCs based on size exclusion (>7 micron) then a trained cytologist identifies CTCs based on the morphological features and the phenotypic expression/lack of expression of EpCAM, Cytokeratins 8, 18, 19, CD45, and DAPI (FIG. 1). Briefly, a low-pressure vacuum with CellSieve™ microfilters, fabricated by lithographic method using photo definable dry film, on a filter holder assembly was placed onto a waste apparatus. The whole peripheral blood (7.5 mL) collected in CellSave preservative tubes™ was prefixed, drawn through the filter (~3 min), washed with PBS, postfixed, and permeabilized. The filter was stained with an antibody cocktail of FITC-labeled anti-Cytokeratin 8, 18, 19; Phycoerythrin (PE)-labeled anti-EpCAM; and Cy5-lableed anti-CD45 antibodies [3, 17, 18]. Filters were washed and slide mounted with Fluoromount-G/DAPI (Southern Biotech). Pathologically definable CTCs (PDCTCs) were morphologically identified using pre-established cytological features as previously described [3]. An Olympus BX54WI Fluorescent microscope with Carl Zeiss AxioCam and Zen2011 Blue (Carl Zeiss) was used to image cells. Fluoromount-G/DAPI is a mounting solution containing DAPI that is added as the last step before adding a cover slip to "mount" the sample. The DAPI signal aggregates and becomes fluorescent in contact with nucleic acids.

Enumerating CTCs. Only intact cells that have pathological definable characteristics (PDCTCs), as previously described [3], were counted as CTCs in this study. This includes CTCs that are CD45 negative, have strong filamentous Cytokeratin signal and have DAPI positive nuclei with malignant pathological criteria. PDCTCs were identified and imaged by a trained cytologist and confirmed by a pathologist [3]. Apoptotic CTCs, CTCs undergoing epithelial to mesenchymal transition (i.e. absence of cytokeratin) and CTCs that could not be cytologically identified as malignant were not included in the study [3, 24].

Grading Mitotic Proliferation. Mitosis was identified by a trained cytologist and confirmed by a pathologist in the CTCs. The nucleic were imaged using an Olympus BX54WI Fluorescent microscope with Carl Zeiss AxioCam and Zen2011 Blue (Carl Zeiss). The stages of active mitosis including prophase, prometaphase, metaphase, anaphase, telophase and cytokinesis, are all well described using both nuclear and cytokeratin structures [5-8]. CTCs were only counted as mitotic if the cytologist could identify the cell as being in a M (mitotic) Phase stage, i.e., one or more of prophase, prometaphase, metaphase, anaphase, telophase and cytokinesis. Otherwise, the CTC was counted as non-mitotic (FIG. 1).

Statistical Methods. Kaplan-Meier estimates and Cox Proportional Hazard regression analyses were made with Matlab R2013A software (Matrix LABoratory; Mathworks, Natick, Mass.) using the enumerated CTC counts from all subtypes and the known patient populations. For survival analysis, the time to death was defined as the interval between when a blood sample was obtained until death, or censored by the last follow up visit. ER (estrogen receptor), PR (progesterone receptor), and HER2 (human epidermal growth factor receptor 2) status were determined according to local guidelines. HER2 was considered positive at a value equal to or greater than 2+ (FIG. 3B and Table 1). Cancer subtype, hormone status, and stage were determined at the time blood was obtained. A power analysis $(1-\beta=0.9, \alpha=0.05)$ determined that a sample size of 30 patients was sufficient to stratify patient cohorts based on previous CTC data analysis [3].

Results. CTCs were found in 83% of patient samples and in none of the healthy control samples, consistent with published studies (i.e., CellSearch® identifies CTCs in ~65%-80% of late stage breast cancer) [1, 2, 4, 19, 20]. The majority of CTCs (~91%), identified by the differential staining of cytokeratin+, DAPI+ and CD45 negative, had a malignant appearance, i.e. high cytoplasmic to nuclear ratios, high pleomorphism, and well-structured filamentous cytokeratin (FIG. 1) [3, 4, 17-20].

Figure 2A:
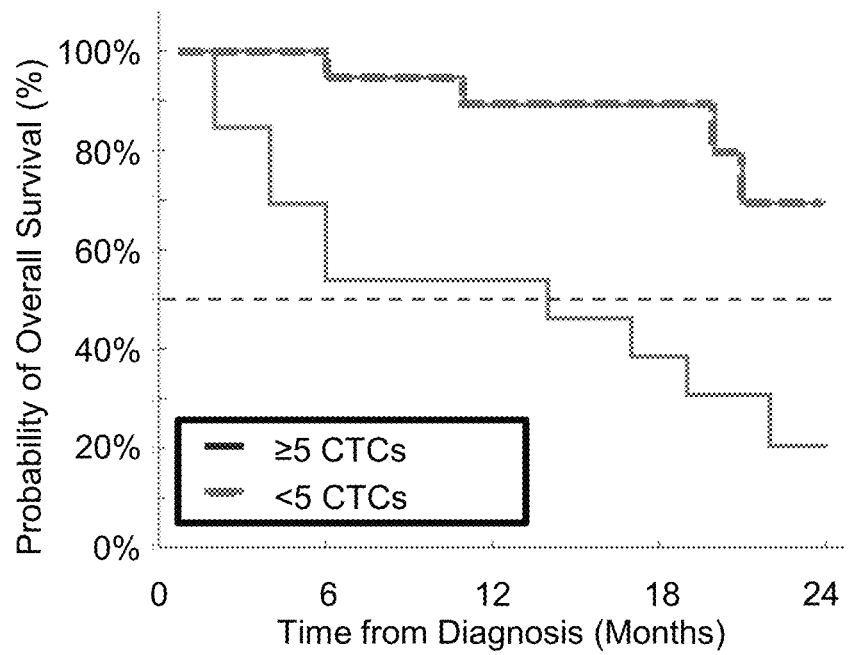
FIGS. 2A-2B. Kaplan-Meier estimates of probabilities of overall survival in the breast cancer patient populations, total CTC count versus mitotic CTC count (n=36).

The patient cohort was divided into subsets using the standard clinical cut off of ≥5 CTCs/sample (samples were 7.5 mL) to determine patient survival [1-4, 17-20]. Specifically, 23 of 36 patients (64%) had <5 CTCs with a median survival of >24 months. Whereas, 13 of 36 patients (36%) had ≥5 CTCs with a median survival of 10.0 months, hazard ratio 5.2 (FIG. 2A and Table 2). This hazard ratio was within the confidence interval of published ratios establishing ≥5 CTCs as the optimal cut off for evaluating patients (i.e., 26-49% of late stage breast cancer patients have ≥5 CTCs per sample with reported median survival ranging from 10.1 to 15 months [1-4, 17-20]).

TABLE 2

| Variable | Number of Patients | Hazard Ratio | 95% CI | p value |
|---|---|---|---|---|
| 1 mitotic CTC vs 0 mitotic CTC | 13 vs 23 | 11.1 | 3.1-39.7 | <0.001 |
| ≥5 CTC vs <5 CTC | 13 vs 23 | 5.17 | 1.6-16.5 | 0.006 |
| ER/PR positive vs negative** | 16 vs 17 | 1.3 | 0.5-3.7 | 0.174 |
| HER2 positive vs negative** | 7 vs 26 | 1.8 | 0.6-5.7 | 0.289 |
| Hormone positive vs triple negative** | 23 vs 10 | 4.0 | 1.4-11.2 | 0.009 |

**Hormone status of three patients cannot be determined

Figure 2B:
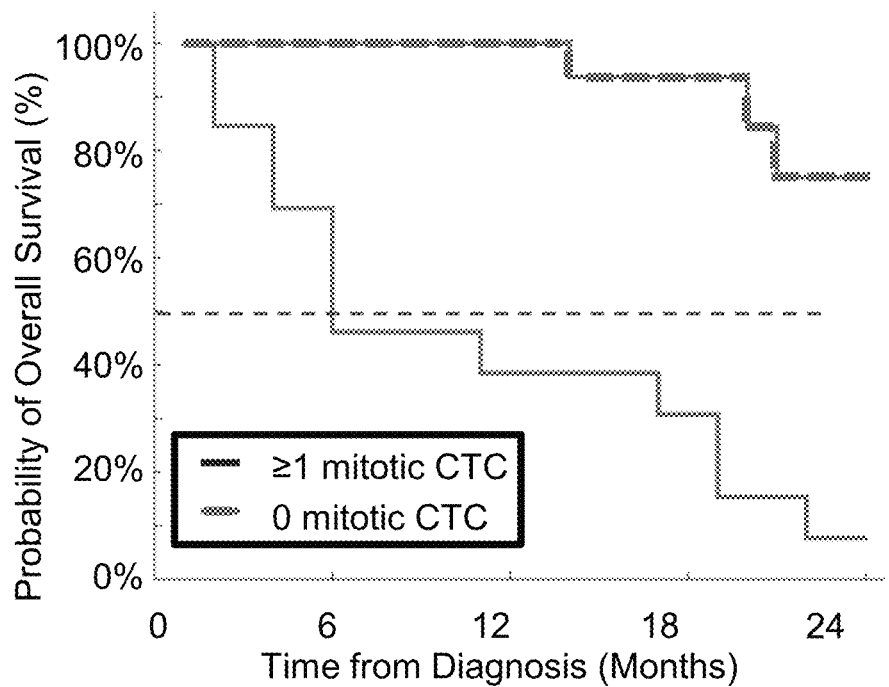
Figure 4:
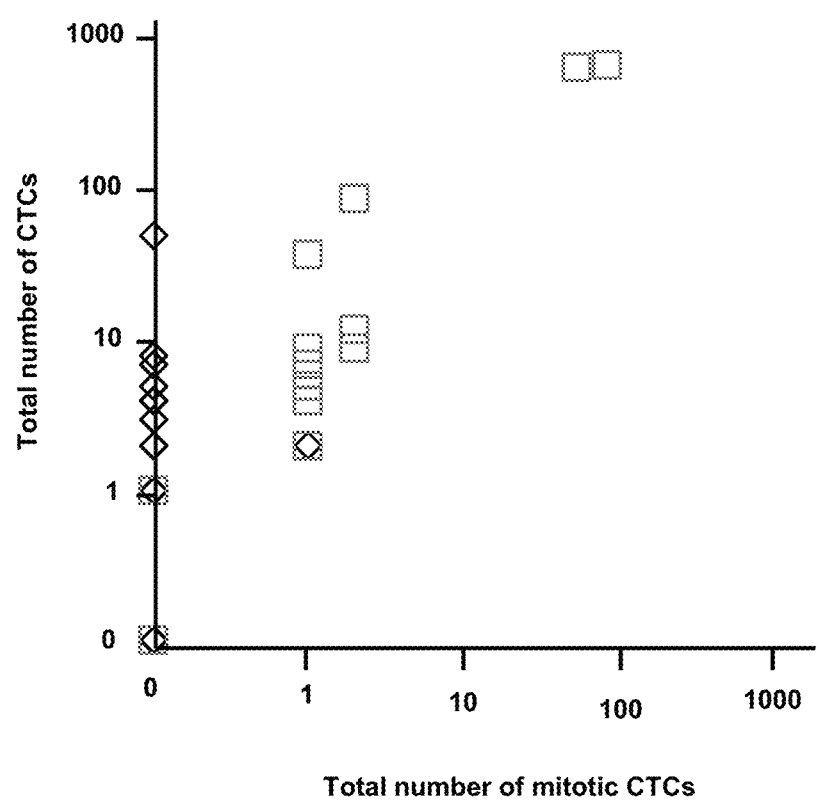
FIG. 4. Box plot of total number of CTCs in each patient versus mitotic CTCs for each patient from 7.5 mL of peripheral blood. Squares=patients expired within 2 years; diamonds=patients alive within 2 years.

All CTCs were then sub-classified based on the cytological identification of M phase phenotypes [1-4, 17-20, 27]. CTCs were identified in all stages of mitosis from the patient cohort, FIG. 1A-1J [5, 6, 8, 27]. Specifically, 23 of 36 patients (64%) had no mitotic CTCs and had a median survival >24 months. In contrast, 13 of 36 patients (36%)

had ≥1 mitotic events, and a median survival of 5.7 months, hazard ratio 11.1 (FIGS. 2B and 4; Table 2). Of note, mitotic events were detected in four patients that had <5 CTCs and were not detected in four patients with ≥5 CTCs (FIG. 4). These data suggest that the additional visual characterization of mitosis in CTCs enhances the stratification of breast cancer patients for prognostic correlation to survival compared with CTC enumeration alone. In the restratified cohort, 92% of patients with at least one mitotic CTC died within the 2 year period of observation versus 13% of patients without a mitotic CTC, representing an 11 fold increase in patient risk (Table 2 and FIG. 2).

Figure 3A:
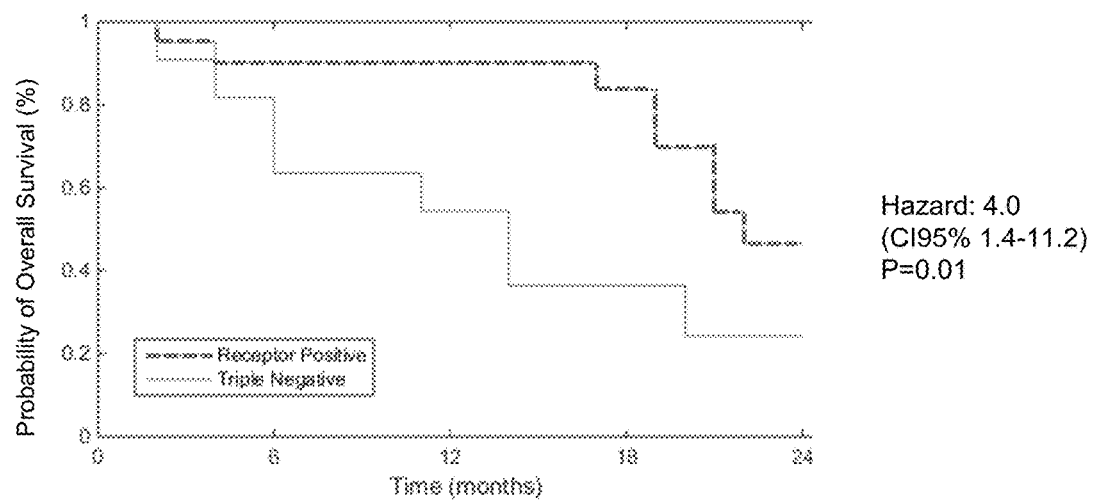
FIGS. 3A-3B. Kaplan-Meier estimates of probabilities of overall survival of the patient subpopulations based on receptor status from FIG. 2A (n=33). Three of the 36 patients did not have a known receptor status. *All hazard ratios were calculated based on the Luminal A patient cohort.
Figure 3B:
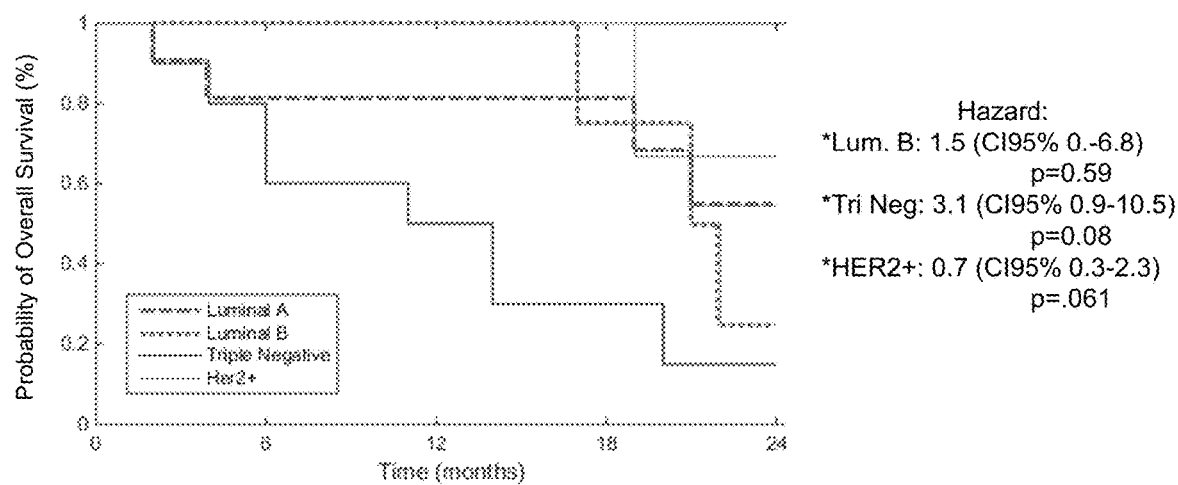

FIG. 3A is a plot of Kaplan-Meier estimates of probabilities of Overall Survival of the patient subpopulations based on receptor status (n=33). Breast cancer are subtyped by receptor status: estrogen receptor (ER), progesterone receptor (PR), human epidermal growth factor receptor 2 (HER2), and triple negative. Three of the 36 patients did not have a known receptor status. FIG. 3B is Kaplan-Meier estimate of probability of Overall Survival of the patient subpopulation based molecular subtypes: Luminal A, Luminal B, HER2 status, and triple negative patients. Luminal A breast cancer subtype is generally characterized as ER-positive and/or PR-positive, HER2-negative, and low Ki67. Luminal B breast cancer subtype is generally characterized as ER-positive and/or PR-positive, HER2-positive (or HER2-negative with high Ki67). The Ki67 molecular marker is an indicator of active cell division in a large number of cancer cells. All hazard ratios were calculated based on the Luminal A patient cohort.

FIG. 4 is a plot of the total number of CTCs in each patient versus mitotic CTCs for each patient from 7.5 mL of peripheral blood. Squares=patients expired after 2 years; diamonds=patients alive after 2 years. In one particular patient, only two CTCs were detected in the sample but one of them was mitotic (MI=0.5). This patient also died within 2 years. These results demonstrate that the number of mitotic CTCs is more important than just total number of CTCs in determining survival. This indicates also mitotic index is more important than CTC count.

Of the 155 identified mitotic events, prophase was the most commonly observed (78% of mitotic CTCs, or 121 cells), followed by telophase/cytokinesis (15%, or 23 cells). Metaphase and anaphase were rarely observed, only 4 in anaphase and 6 in metaphase, 2.6% and 3.9%, respectively. Interestingly, the number of mitotic events was more common than expected, 9.3% of all CTCs.

Using a sample size sufficient to properly stratify the patient cohort, these results demonstrate that while CTC number is in fact a prognostic indicator of patient survival, by subtyping the same population based on CTCs in cytological mitosis, the hazard increased dramatically to 11.1. Using cytological assessment of CTCs, combined with the calculated patient survival, these observations imply that there are quantifiable populations of intact CTCs in mitosis found outside the tumor area, which could be the sought after, clinically relevant CTC populations. While it cannot be determined whether these CTCs are actively dividing in circulation or that dividing CTCs are simply breaking off the tumor into the circulatory system, the finding of these cells in late stage breast cancer is intriguing. Considering that mitotic cells are less stable and prone to structural collapse, the stress of circulation should intuitively lessen the frequency of mitotic CTCs and destroy the cells before isolation, which did not occur [5-8]. Biologically, these events hint at aggressive cellular subtypes involved in the metastatic cascade, and the observations present here imply that there are quantifiable populations of CTCs in the mitotic phase found outside the tumor area.

Despite being a small cohort, the patient population represented a heterogeneous group of breast cancers with diverse hormone status (Tables 1 & 2) and distinct cohort separation, indicating the possible applications to breast cancer in general, and even other forms of cancer. The presence of mitotic CTCs, and the association with increases risk, indicates the existence of a statistically significant cohort with an aggressive cancer subtype.

Tracking of mitotic cancer cells transiting the circulatory system provides a simple, non-invasive method to gather clinically relevant information on highly aggressive tumor cells that can aid in planning patient treatment as a tumor progression evolves. While tumor 'omics profiling promises a future of personalized treatment medicine, currently, spread of disease (i.e. stage) followed by aggressiveness of disease (i.e. grade) remain the first and second most important factors in patients survival and treatment. Incorporating mitotic indices into CTC assessment might better stratify patients into prognostic groups, better inform a physician of tumor evolution, and identify the more aggressive cancer targets using a blood based biopsy.

Further, assaying for the number of CTCs in the mitotic phase, as well as a change in the number of CTCs in the mitotic phase over time, provides clinically useful information that can be used to determine which treatment to administer to a patient, whether the patient will response to a particular treatment, and whether the patient is responding during or after a course of treatment. CTC mitotic phase is thus also a predictor of response to treatment. For example, an increase in the number of mitotic CTCs may be an indication that the patient is not responding to treatment. Similarly, an increase in the mitotic index may also be an indication that the patient is not responding to treatment.

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

1. Febbo P G, Ladanyi M, Aldape K D, De Marzo A M, Hammond M E, Hayes D F, Iafrate A J, Kelley R K, Marcucci G, Ogino S et al: NCCN Task Force report: Evaluating the clinical utility of tumor markers in oncology. Journal of the National Comprehensive Cancer Network: JNCCN 2011, 9 Suppl 5:S1-32; quiz S33.
2. Smerage J B, Barlow W E, Hortobagyi G N, Winer E P, Leyland-Jones B, Srkalovic G, Tejwani S, Schott A F, O'Rourke M A, Lew D L et al: Circulating tumor cells and response to chemotherapy in metastatic breast cancer: SWOG 50500. Journal of Clinical Oncology 2014, 32(31):3483-3489.
3. Adams D L, Stefansson S, Haudenschild C, Martin S S, Charpentier M, Chumsri S, Cristofanilli M, Tang C M, Alpaugh R K: Cytometric characterization of circulating tumor cells captured by microfiltration and their correlation to the CellSearch® CTC test. Cytometry Part A: the journal of the International Society for Analytical Cytology 2015, 87(2):137-144.
4. Allard W J, Matera J, Miller M C, Repollet M, Connelly M C, Rao C, Tibbe A G, Uhr J W, Terstappen L W: Tumor cells circulate in the peripheral blood of all major carcinomas but not in healthy subjects or patients with non-malignant diseases. Clinical cancer research: an official journal of the American Association for Cancer Research 2004, 10(20):6897-6904.
5. Bloom H J, Richardson W W: Histological grading and prognosis in breast cancer; a study of 1409 cases of which 359 have been followed for 15 years. British journal of cancer 1957, 11(3):359-377.
6. Clayton F: Pathologic correlates of survival in 378 lymph node-negative infiltrating ductal breast carcinomas. Mitotic count is the best single predictor. Cancer 1991, 68(6):1309-1317.
7. Galea M H, Blamey R W, Elston C E, Ellis I O: The Nottingham Prognostic Index in primary breast cancer. Breast cancer research and treatment 1992, 22(3):207-219.
8. National Comprehensive Cancer N: Breast Cancer Screening and Diagnosis Clinical Practice Guidelines in Oncology. Journal of the National Comprehensive Cancer Network: JNCCN 2003, 1(2):242-263.
9. Dalton L W, Pinder S E, Elston C E, Ellis I O, Page D L, Dupont W D, Blarney R W: Histologic grading of breast cancer: linkage of patient outcome with level of pathologist agreement. Modern pathology: an official journal of the United States and Canadian Academy of Pathology, Inc 2000, 13(7):730-735.
10. Burton J L, Goepel J R, Lee J A: Demand management in urine cytology: a single cytospin slide is sufficient. Journal of clinical pathology 2000, 53(9):718-719.
11. Stott S L, Lee R J, Nagrath S, Yu M, Miyamoto D T, Ulkus L, Inserra E J, Ulman M, Springer S, Nakamura Z et al: Isolation and characterization of circulating tumor cells from patients with localized and metastatic prostate cancer. Science translational medicine 2010, 2(25): 25ra23.
12. Paoletti C, Muniz M C, Thomas D G, Griffith K A, Kidwell K M, Tokudome N, Brown M E, Aung K, Miller M C, Blossom D L et al: Development of circulating tumor cell-endocrine therapy index in patients with hormone receptor-positive breast cancer. Clinical cancer research: an official journal of the American Association for Cancer Research 2015, 21(11):2487-2498.
13. Jonat W, Arnold N: Is the Ki-67 labelling index ready for clinical use? Annals of oncology: official journal of the European Society for Medical Oncology/ESMO 2011, 22(3):500-502.
14. Colozza M, Sidoni A, Piccart-Gebhart M: Value of Ki67 in breast cancer: the debate is still open. The Lancet Oncology 2010, 11(5):414-415.
15. Serrano M J, Nadal R, Lorente J A, Salido M, Rodriguez R, Rodriguez M, Macia M, Sanchez-Rovira P, Corominas J M, Gonzalez L et al: Circulating cancer cells in division in an early breast cancer patient. Annals of oncology: official journal of the European Society for Medical Oncology/ESMO 2011, 22(9):2150-2151.
16. Andre F, Arnedos M, Goubar A, Ghouadni A, Delaloge S: Ki67-no evidence for its use in node-positive breast cancer. Nature reviews Clinical oncology 2015, 12(5):296-301.
17. Adams D L, Martin S S, Alpaugh R K, Charpentier M, Tsai S, Bergan R C, Ogden I M, Catalona W, Chumsri S, Tang C M et al: Circulating giant macrophages as a potential biomarker of solid tumors. Proceedings of the National Academy of Sciences of the United States of America 2014, 111(9):3514-3519.
18. Adams D L, Zhu P, Makarova O V, Martin S S, Charpentier M, Chumsri S, Li S, Amstutz P, Tang C M: The systematic study of circulating tumor cell isolation using lithographic microfilters. RSC advances 2014, 9:4334-4342.
19. Cristofanilli M, Budd G T, Ellis M J, Stopeck A, Matera J, Miller M C, Reuben J M, Doyle G V, Allard W J, Terstappen L W et al: Circulating tumor cells, disease progression, and survival in metastatic breast cancer. The New England journal of medicine 2004, 351(8):781-791.
20. Miller M C, Doyle G V, Terstappen L W: Significance of Circulating Tumor Cells Detected by the CellSearch System in Patients with Metastatic Breast Colorectal and Prostate Cancer. Journal of oncology 2010, 2010:617421.
21. Ferreira M M, Ramani V C, Jeffrey S S: Circulating Tumor Cell Technologies. Molecular Oncology 2016.
22. Lianidou E S, Markou A: Circulating tumor cells in breast cancer: detection systems, molecular characterization, and future challenges. Clinical chemistry 2011, 57(9):1242-1255.
23. Low W S, Abas W A B W: Benchtop Technologies for Circulating Tumor Cells Separation Based on Biophysical Properties. BioMed Research International 2015, 2015.
24. Adams D L, Alpaugh R K, Martin S S, Charpentier M, Chumsri S, Cristofanilli M, Adams D K, Makarova O V, Zhu P, Li S et al: Precision microfilters as an all in one system for multiplex analysis of circulating tumor cells. RSC advances 2016, 6(8):6405-6414.
25. Idowu M O, Powers C N: Lung cancer cytology: potential pitfalls and mimics—a review. International journal of clinical and experimental pathology 2010, 3(4):367-385.
26. Deisenhammer F, Bartos A, Egg R, Gilhus N E, Giovannoni G, Rauer S, Sellebjerg F, Force E T: Guidelines on routine cerebrospinal fluid analysis. Report from an EFNS task force. European journal of neurology: the official journal of the European Federation of Neurological Societies 2006, 13(9):913-922.
27. Devenport D, Oristian D, Heller E, Fuchs E: Mitotic internalization of planar cell polarity proteins preserves tissue polarity. Nature cell biology 2011, 13(8):893-902.
28. Polzer B, Medoro G, Pasch S, Fontana F, Zorzino L, Pestka A, Andergassen U, Meier-Stiegen F, Czyz Z T, Alberter B et al: Molecular profiling of single circulating tumor cells with diagnostic intention. EMBO molecular medicine 2014, 6(11):1371-1386.
29. Lohr J G, Adalsteinsson V A, Cibulskis K, Choudhury A D, Rosenberg M, Cruz-Gordillo P, Francis J M, Zhang C Z, Shalek A K, Satija R et al: Whole-exome sequencing of circulating tumor cells provides a window into metastatic prostate cancer. Nature biotechnology 2014, 32(5):479-484.

What is claimed is:
1. A method for predicting likelihood of survival of a subject having cancer, wherein the method comprises:
(a) obtaining a population of circulating tumor cells (CTCs) from a biological sample of the subject having cancer,
(b) screening the population of CTCs for cells in a mitotic cell cycle phase, and
(c) identifying CTCs in a mitotic cell cycle phase, and

(d) administering an appropriate course of cancer treatment to the subject either before or after the population of CTCs is so identified in (c);
wherein when one or more CTCs is identified as being in a mitotic cell cycle phase, the subject is predicted to have a lower likelihood of survival in comparison to a subject having the same cancer that does not have one or more CTCs identified as being in a mitotic cell cycle phase, thereby predicting likelihood of survival of a subject having cancer.

2. The method of claim 1, wherein the biological sample is selected from the group consisting of peripheral blood, blood, lymph nodes, bone marrow, cerebral spinal fluid, and urine.

3. The method of claim 1, wherein the biological sample is at least about 7.5 mL of peripheral blood.

4. The method of claim 1, wherein the cancer is carcinoma and the CTCs are characterized by one or more of the following characteristics:
(a) diameter of between about 7 and 25 microns,
(b) presence of one or more markers selected from the group consisting of cytokeratin (CK) 8, CK18, CK19, and EpCAM, and
(c) absence of one or more markers selected from the group consisting of CD45, CD14, and CD31.

5. The method of claim 4, wherein the CTCs are further characterized by presence of one or more markers selected from the group consisting of EGFR, HER2, MUC-1, EphB4, CEA, CK5, CK6, CK7, CK14, CK16, CK17, CK20, PLZ4, PSMA, PSA, PDX-1, CXCR-4, and CDX2.

6. The method of claim 4, wherein the carcinoma is a breast, prostate, lung, colorectal or pancreatic tumor, and wherein CTCs are characterized by the following characteristics:
(a) diameter of between about 7 and 25 microns,
(b) presence of CK8, CK18, CK19, and EpCAM, and
(c) absence of CD45.

7. The method of claim 1, wherein the cancer is melanoma and the CTCs are characterized by one or more of the following characteristics:
(a) diameter of between about 7 and 25 microns, and
(b) presence of one or more markers selected from the group consisting of CD 146, Melanin, PAX3d, MLANA, TGFp2, MCAM, ABCB4, CSPG4, MART-1, MAGE-A3, and GAINAc-T.

8. The method of claim 1, wherein the cancer is sarcoma and the CTCs are characterized by one or more of the following characteristics:
(a) diameter of between about 7 and 25 microns, and
(b) presence of vimentin.

9. The method of claim 1, wherein the cancer is renal cell carcinoma and the CTCs are characterized by one or more of the following characteristics:
(a) diameter of between about 7 and 25 microns, and
(b) presence of one or more markers selected from the group consisting of vimentin, CD 10, CK8, CK18, CK19, c-Kit, and E-cadherin.

10. The method of claim 1, wherein the mitotic cell cycle phase is determined by staining the cells with a nuclear stain and visually determining the cell cycle phase.

11. The method of claim 1, wherein the likelihood of survival is over a two year period and wherein the biological sample is at least about 7.5 mL of peripheral blood.

12. A method for grading a malignant solid tumor in a subject, wherein the method comprises:
(a) obtaining a population of CTCs from a biological sample of a subject having a malignant solid tumor,
(b) screening the population of CTCs for cells in a mitotic cell cycle phase,
(c) identifying CTCs in a mitotic cell cycle phase, and
(d) administering an appropriate course of cancer treatment to the subject either before or after the population of CTCs is obtained from the subject,
wherein when one or more CTCs is identified as being in a mitotic cell cycle phase, the tumor of the subject is graded as aggressive, thereby grading a malignant solid tumor in a subject.

13. The method of claim 12, wherein the biological sample is selected from the group consisting of peripheral blood, blood, lymph nodes, bone marrow, cerebral spinal fluid, and urine.

14. The method of claim 12, wherein the biological sample is at least about 7.5 mL of peripheral blood.

15. The method of claim 12, wherein the malignant solid tumor is carcinoma and the CTCs are characterized by one or more of the following characteristics:
(a) diameter of between about 7 and 25 microns,
(b) presence of one or more markers selected from the group consisting of cytokeratin (CK) 8, CK18, CK19, and EpCAM, and
(c) absence of one or more markers selected from the group consisting of CD45, CD14, and CD31.

16. The method of claim 15, wherein the CTCs are further characterized by presence of one or more markers selected from the group consisting of EGFR, HER2, MUC-1, EphB4, CEA, CK5, CK6, CK7, CK14, CK16, CK17, CK20, PLZ4, PSMA, PSA, PDX-1, CXCR-4, and CDX2.

17. The method of claim 15, wherein the carcinoma is a breast, prostate, lung, colorectal or pancreatic tumor, and wherein CTCs are characterized by the following characteristics:
(a) diameter of between about 7 and 25 microns,
(b) presence of CK8, CK18, CK19, and EpCAM, and
(c) absence of CD45.

18. The method of claim 12, wherein the malignant solid tumor is melanoma and the CTCs are characterized by one or more of the following characteristics:
(a) diameter of between about 7 and 25 microns, and
(b) presence of one or more markers selected from the group consisting of CD 146, Melanin, PAX3d, MLANA, TGFp2, MCAM, ABCB4, CSPG4, MART-1, MAGE-A3, and GAINAc-T.

19. The method of claim 12, wherein the malignant solid tumor is sarcoma and the CTCs are characterized by one or more of the following characteristics:
(a) diameter of between about 7 and 25 microns, and
(b) presence of vimentin.

20. The method of claim 12, wherein the malignant solid tumor is renal cell carcinoma and the CTCs are characterized by one or more of the following characteristics:
(a) diameter of between about 7 and 25 microns, and
(b) presence of one or more markers selected from the group consisting of vimentin, CD 10, CK8, CK18, CK19, c-Kit, and E-cadherin.

21. The method of claim 12, wherein the mitotic cell cycle phase is determined by staining the cells with a nuclear stain and visually determining the cell cycle phase.

* * * * *